United States Patent
Brannan et al.

(10) Patent No.: US 9,028,474 B2
(45) Date of Patent: May 12, 2015

(54) MICROWAVE SURFACE COAGULATOR WITH RETRACTABLE BLADE

(75) Inventors: Joseph D. Brannan, Erie, CO (US); Casey M. Ladtkow, Westminster, CO (US)

(73) Assignee: Covidien LP, Mansfield, MA (US)

( * ) Notice: Subject to any disclaimer, the term of this patent is extended or adjusted under 35 U.S.C. 154(b) by 1015 days.

(21) Appl. No.: 12/731,367

(22) Filed: Mar. 25, 2010

(65) Prior Publication Data
US 2011/0238053 A1    Sep. 29, 2011

(51) Int. Cl.
| A61B 18/18 | (2006.01) |
| A61B 17/3211 | (2006.01) |
| A61B 18/00 | (2006.01) |

(52) U.S. Cl.
CPC ......... *A61B 18/1815* (2013.01); *A61B 17/3211* (2013.01); *A61B 2017/32113* (2013.01); *A61B 2018/00023* (2013.01); *A61B 2018/1861* (2013.01)

(58) Field of Classification Search
CPC .................. A61B 18/1815; A61B 2018/1861; A61B 2018/1884; A61B 2018/1892
USPC ...................................... 606/32–52, 205–207
See application file for complete search history.

(56) References Cited

U.S. PATENT DOCUMENTS

| D263,020 S | 2/1982 | Rau, III |
| 4,534,347 A | 8/1985 | Taylor |
| D295,893 S | 5/1988 | Sharkany et al. |
| D295,894 S | 5/1988 | Sharkany et al. |
| 4,949,734 A | 8/1990 | Bernstein |
| 5,344,424 A | 9/1994 | Roberts et al. |
| 5,431,672 A | 7/1995 | Cote et al. |
| 5,908,432 A | 6/1999 | Pan |
| D424,694 S | 5/2000 | Tetzlaff et al. |
| D425,201 S | 5/2000 | Tetzlaff et al. |
| D449,886 S | 10/2001 | Tetzlaff et al. |
| D457,958 S | 5/2002 | Dycus et al. |

(Continued)

FOREIGN PATENT DOCUMENTS

| DE | 390937 | 3/1924 |
| DE | 1099658 | 2/1961 |

(Continued)

OTHER PUBLICATIONS

U.S. Appl. No. 08/483,742, filed Jun. 7, 1995.

(Continued)

*Primary Examiner* — Ronald Hupczey, Jr.

(57) ABSTRACT

An ablation instrument having an ergonomic handle that includes an actuator adapted to selectively extend and retract a blade that is pivotably mounted within an aperture assembly coupled to the housing by a shaft. The shaft extends distally from the handle and includes a coaxial feedline, a wire conduit disposed along a longitudinal axis of the shaft, and a pull wire disposed within the wire conduit and having a proximal and a distal end, wherein a proximal end of the pull wire is operably coupled to the actuator. The aperture assembly is coupled to a distal end of the shaft and includes a reflector having a closed upper portion, and an open lower portion from which the blade may be extended for use. Also disclosed is an ablation system that includes the above-described ablation instrument, a source of ablation energy, and optionally, a source of coolant for cooling the shaft and aperture assembly.

20 Claims, 9 Drawing Sheets

(56) References Cited

U.S. PATENT DOCUMENTS

| | | | |
|---|---|---|---|
| D457,959 S | 5/2002 | Tetzlaff et al. | |
| D496,997 S | 10/2004 | Dycus et al. | |
| D499,181 S | 11/2004 | Dycus et al. | |
| 6,860,880 B2 | 3/2005 | Treat et al. | |
| 7,033,356 B2 | 4/2006 | Latterell et al. | |
| D525,361 S | 7/2006 | Hushka | |
| D531,311 S | 10/2006 | Guerra et al. | |
| 7,131,970 B2 * | 11/2006 | Moses et al. | 606/51 |
| D533,942 S | 12/2006 | Kerr et al. | |
| D535,027 S | 1/2007 | James et al. | |
| D541,418 S | 4/2007 | Schechter et al. | |
| 7,204,832 B2 | 4/2007 | Altshuler et al. | |
| D541,938 S | 5/2007 | Kerr et al | |
| 7,326,205 B2 | 2/2008 | Paul et al. | |
| D564,662 S | 3/2008 | Moses et al. | |
| 7,419,488 B2 | 9/2008 | Ciarrocca et al. | |
| 7,488,319 B2 * | 2/2009 | Yates | 606/51 |
| 8,313,483 B2 * | 11/2012 | Hosaka et al. | 606/33 |
| 2002/0019631 A1 | 2/2002 | Kidder et al. | |
| 2002/0120261 A1 | 8/2002 | Morris et al. | |
| 2005/0096645 A1 | 5/2005 | Wellman et al. | |
| 2005/0096646 A1 | 5/2005 | Wellman et al. | |
| 2005/0149010 A1 * | 7/2005 | Turovskiy et al. | 606/33 |
| 2005/0245920 A1 | 11/2005 | Vitullo et al. | |
| 2006/0259035 A1 * | 11/2006 | Nezhat et al. | 606/50 |
| 2007/0016182 A1 | 1/2007 | Lipson et al. | |
| 2009/0254092 A1 | 10/2009 | Albiol Llorach | |
| 2010/0249769 A1 * | 9/2010 | Nau et al. | 606/33 |
| 2011/0040300 A1 * | 2/2011 | Brannan | 606/41 |
| 2011/0077633 A1 * | 3/2011 | Bonn et al. | 606/33 |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| FR | 179 607 | 11/1906 |
| FR | 1 275 415 | 9/1960 |
| FR | 1 347 865 | 11/1963 |
| FR | 2 276 027 | 6/1974 |
| FR | 2 235 669 | 1/1975 |
| FR | 2 313 708 | 12/1976 |
| FR | 2 502 935 | 10/1982 |
| FR | 2 517 953 | 6/1983 |
| FR | 2 573 301 | 11/1984 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| JP | 2008142467 | 6/2008 |
| SU | 166452 | 11/1964 |
| SU | 401367 | 11/1974 |
| SU | 727201 | 4/1980 |
| WO | WO 01/95810 | 12/2001 |

OTHER PUBLICATIONS

U.S. Appl. No. 08/136,098, filed Oct. 14, 1993.
U.S. Appl. No. 12/199,935, filed Aug. 28, 2008.
U.S. Appl. No. 12/203,474, filed Sep. 3, 2008.
U.S. Appl. No. 12/236,686, filed Sep. 24, 2008.
U.S. Appl. No. 12/244,850, filed Oct. 10, 2008.
U.S. Appl. No. 12/250,110, filed Oct. 13, 2008.
U.S. Appl. No. 12/250,171, filed Oct. 13, 2008.
U.S. Appl. No. 12/251,857, filed Oct. 15, 2008.
U.S. Appl. No. 12/253,457, filed Oct. 17, 2008.
U.S. Appl. No. 12/389,906, filed Feb. 20, 2009.
U.S. Appl. No. 12/389,915, filed Feb. 20, 2009.
U.S. Appl. No. 12/401,268, filed Mar. 10, 2009.
U.S. Appl. No. 12/416,583, filed Apr. 1, 2009.
U.S. Appl. No. 12/419,395, filed Apr. 7, 2009.
U.S. Appl. No. 12/423,609, filed Apr. 14, 2009.
U.S. Appl. No. 12/436,237, filed May 6, 2009.
U.S. Appl. No. 12/436,239, filed May 6, 2009.
U.S. Appl. No. 12/436,231, filed May 6, 2009.
U.S. Appl. No. 12/472,831, filed May 27, 2009.
U.S. Appl. No. 12/475,082, filed May 29, 2009.
U.S. Appl. No. 12/476,960, filed Jun. 2, 2009.
U.S. Appl. No. 12/487,917, filed Jun. 19, 2009.
U.S. Appl. No. 12/493,302, filed Jun. 29, 2009.
U.S. Appl. No. 12/504,738, filed Jul. 17, 2009.
U.S. Appl. No. 12/535,851, filed Aug. 5, 2009.
U.S. Appl. No. 12/535,856, filed Aug. 5, 2009.
U.S. Appl. No. 12/536,616, filed Aug. 6, 2009.
U.S. Appl. No. 12/542,348, filed Aug. 17, 2009.
U.S. Appl. No. 12/542,785, filed Aug. 18, 2009.
U.S. Appl. No. 12/547,155, filed Aug. 25, 2009.
U.S. Appl. No. 12/548,644, filed Aug. 27, 2009.
U.S. Appl. No. 12/555,576, filed Sep. 8, 2009.
U.S. Appl. No. 12/556,010, filed Sep. 9, 2009.
U.S. Appl. No. 12/561,096, filed Sep. 16, 2009.
U.S. Appl. No. 12/562,575, filed Sep. 18, 2009.
U.S. Appl. No. 12/562,842, filed Sep. 18, 2009.
U.S. Appl. No. 12/566,299, filed Sep. 24, 2009.
U.S. Appl. No. 12/568,067, filed Sep. 28, 2009.

(56) References Cited

OTHER PUBLICATIONS

U.S. Appl. No. 12/568,524, filed Sep. 28, 2009.
U.S. Appl. No. 12/568,551, filed Sep. 28, 2009.
U.S. Appl. No. 12/568,777, filed Sep. 29, 2009.
U.S. Appl. No. 12/568,838, filed Sep. 29, 2009.
U.S. Appl. No. 12/568,883, filed Sep. 29, 2009.
U.S. Appl. No. 12/568,972, filed Sep. 29, 2009.
U.S. Appl. No. 12/569,171, filed Sep. 29, 2009.
U.S. Appl. No. 12/569,685, filed Sep. 29, 2009.
U.S. Appl. No. 12/582,857, filed Oct. 21, 2009.
U.S. Appl. No. 12/606,769, filed Oct. 27, 2009.
U.S. Appl. No. 12/607,221, filed Oct. 28, 2009.
U.S. Appl. No. 12/607,268, filed Oct. 28, 2009.
U.S. Appl. No. 12/619,462, filed Nov. 16, 2009.
U.S. Appl. No. 12/620,289, filed Nov. 17, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/ Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw•Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 1 0-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical lmpedence" Am. J. MI, Jan. Mar. 1964, pp. 16-27.
Goldberg et al., "Image-guided Radiofrequency Tumor Ablation: Challenges and Opportunities—Part I", (2001) J Vasc. lnterv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite•Element Codes to Model Electrical Heating and Non•Linear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.

(56) References Cited

OTHER PUBLICATIONS

Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTech product literature (Dec. 1999) "FlexStrand": product description, 1 page.
MDTech product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.

Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l, Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al.; "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
Urologix, Inc.—Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 03721482 dated Feb. 6, 2006.
European Search Report EP 04009964 dated. Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.

(56) References Cited

OTHER PUBLICATIONS

European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09166708 dated Oct. 15, 2009.
European Search Report EP 09169376.2 extended dated Dec. 16, 2009.
European Search Report EP 09172838.6 extended dated Jan. 20, 2010.
European Search Report EP 09173268.5 extended dated Jan. 27, 2010.
International Search Report PCT/US98/18640 dated Jan. 29, 1998.
International Search Report PCT/US98/23950 dated Jan. 14, 1998.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.
European Search Report for Application No. 11 00 2476 dated Jul. 7, 2011.

* cited by examiner

A-A

B-B

MICROWAVE SURFACE COAGULATOR WITH RETRACTABLE BLADE

BACKGROUND

1. Technical Field

The present disclosure relates to systems and methods for providing energy to biologic tissue and, more particularly, to an electrosurgical instrument for performing surface coagulation and dissection of biologic tissue.

2. Background of Related Art

Energy-based tissue treatment is well known in the art. Various types of energy (e.g., electrical, ultrasonic, microwave, cryogenic, thermal, laser, etc.) are applied to tissue to achieve a desired result. Electrosurgery involves application of high radio frequency electrical current to a surgical site to cut, ablate, coagulate or seal tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated. A patient return electrode is placed remotely from the active electrode to carry the current back to the generator. In tissue ablation electrosurgery, the radio frequency energy may be delivered to targeted tissue by an antenna or probe.

There are several types of microwave antenna assemblies in use, e.g., monopole, dipole and helical, which may be used in tissue ablation applications. In monopole and dipole antenna assemblies, microwave energy generally radiates perpendicularly away from the axis of the conductor. Monopole antenna assemblies typically include a single, elongated conductor. A typical dipole antenna assembly includes two elongated conductors, which are linearly aligned and positioned end-to-end relative to one another with an electrical insulator placed therebetween. Helical antenna assemblies include a helically-shaped conductor connected to a ground plane. Helical antenna assemblies can operate in a number of modes including normal mode (broadside), in which the field radiated by the helix is maximum in a perpendicular plane to the helix axis, and axial mode (end fire), in which maximum radiation is along the helix axis. The tuning of a helical antenna assembly may be determined, at least in part, by the physical characteristics of the helical antenna element, e.g., the helix diameter, the pitch or distance between coils of the helix, and the position of the helix in relation to the probe assembly to which it is mounted.

The typical microwave antenna has a long, thin inner conductor that extends along the longitudinal axis of the probe and is surrounded by a dielectric material and is further surrounded by an outer conductor around the dielectric material such that the outer conductor also extends along the axis of the probe. In another variation of the probe that provides for effective outward radiation of energy or heating, a portion or portions of the outer conductor can be selectively removed. This type of construction is typically referred to as a "leaky waveguide" or "leaky coaxial" antenna. Another variation on the microwave probe involves having the tip formed in a uniform spiral pattern, such as a helix, to provide the necessary configuration for effective radiation. This variation can be used to direct energy in a particular direction, e.g., perpendicular to the axis, in a forward direction (i.e., towards the distal end of the antenna), or combinations thereof. In the case of tissue ablation, a high radio frequency electrical current in the range of about 500 MHz to about 10 GHz is applied to a targeted tissue site to create an ablation volume, which may have a particular size and shape. Ablation volume is correlated to antenna design, antenna tuning, antenna impedance and tissue impedance.

Certain surgical procedures require use of a cutting instrument, e.g., a scalpel or shears, to resect tumors and/or other necrotic lesions, which may necessitate severing one or more blood vessels and thus cause undesirable bleeding. Such bleeding may, in turn, obscure a surgeon's view of the surgical site and generally require the surgeon to attend to controlling the bleeding, rather than to the primary surgical objective (s). This, in turn, may lead to increased operative times and suboptimal surgical outcomes.

SUMMARY

The present disclosure is directed to a surgical instrument utilizing microwave energy for simultaneous coagulation and dissection of tissue. The instrument may be a handheld surgical device having an elongated shaft. The distal end of the shaft includes a directional microwave aperture having a selectively retractable blade adapted to dissect tissue. The proximal end of the shaft may include a handle and one or more actuators, e.g., a pushbutton adapted to activate the delivery of coagulation energy, and/or a handle adapted to control the position of a retractable scalpel, or cutting blade. Ablation energy is provided to the microwave aperture by a coaxial feed line disposed within the elongated shaft.

The microwave aperture may have a hemispherical shape, an elongated cup shape, a clamshell shape, a cylindrical shape, a rounded cylindrical shape, a parabolic shape, and/or various combinations thereof. The aperture includes metallic boundaries on all but one side, which may be an open bottom. A non-metallic bottom cover is fixed to the open bottom of the aperture and is formed from RF-transparent material. During use, the RF-transparent bottom cover is positioned at the operative site, and may be in contact with targeted tissue. Ablation energy is introduced into the interior region of the reflector, where it is directed though the bottom cover to coagulate tissue. The disclosed instrument also provides the ability to concurrently extend the cutting blade to resect and/ or dissect the targeted tissue. The use of a retractable blade with the concurrent application of coagulation energy enables a surgeon to perform dissection using the blade, while simultaneously performing coagulation on the tissue, to control or eliminate bleeding at the operative site. Used in this manner, a surgical instrument in accordance with an embodiment of the present disclosure may reduce operative times, decrease risk factors, shorten recovery times, and improve patient outcomes.

Also disclosed is a surgical instrument comprising a housing having an actuator adapted to operably engage a proximal end of a pull wire. The instrument includes a shaft that extends distally from the housing to an aperture assembly at a distal end of the shaft. The shaft includes a coaxial feedline having an inner conductor, an outer conductor disposed coaxially about the inner conductor, a wire conduit disposed along a longitudinal axis of the shaft, and a pull wire disposed within the wire conduit. The pull wire includes a proximal end and a distal end, wherein the proximal end of the pull wire is operably coupled to the actuator. The instrument includes an aperture assembly coupled to a distal end of the shaft. The aperture assembly includes a reflector having a closed upper portion and an open lower portion, a radiating section disposed within the reflector and operably coupled to the inner conductor, a blade pivotably mounted within the reflector and pivotable between at least a closed position and an open position. The distal end of the pull wire is operably coupled to the blade to facilitate the extension and retraction thereof. A substantially planar bottom cover encloses the open lower portion of the reflector.

In embodiments, the instrument includes a generally tubular divider within the shaft that is concentrically disposed between the inner conductor and the outer conductor to form an inflow conduit and an outflow conduit. A distal opening of at least one of the inflow conduit and the outflow conduit are in fluid communication with an internal volume of the reflector. During use, a proximal end of the inflow conduit may be operably coupled to source of coolant for cooling the shaft and/or the aperture assembly. Coolant may be circulated from the source of coolant, distally through the inflow conduit in the shaft, into an internal volume of the reflector, proximally through the outflow conduit, and evacuated from the instrument.

Also disclosed is a surgical ablation system that includes a source of microwave ablation energy, and, optionally, a source of coolant, that is operably coupled to the aforesaid instrument.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
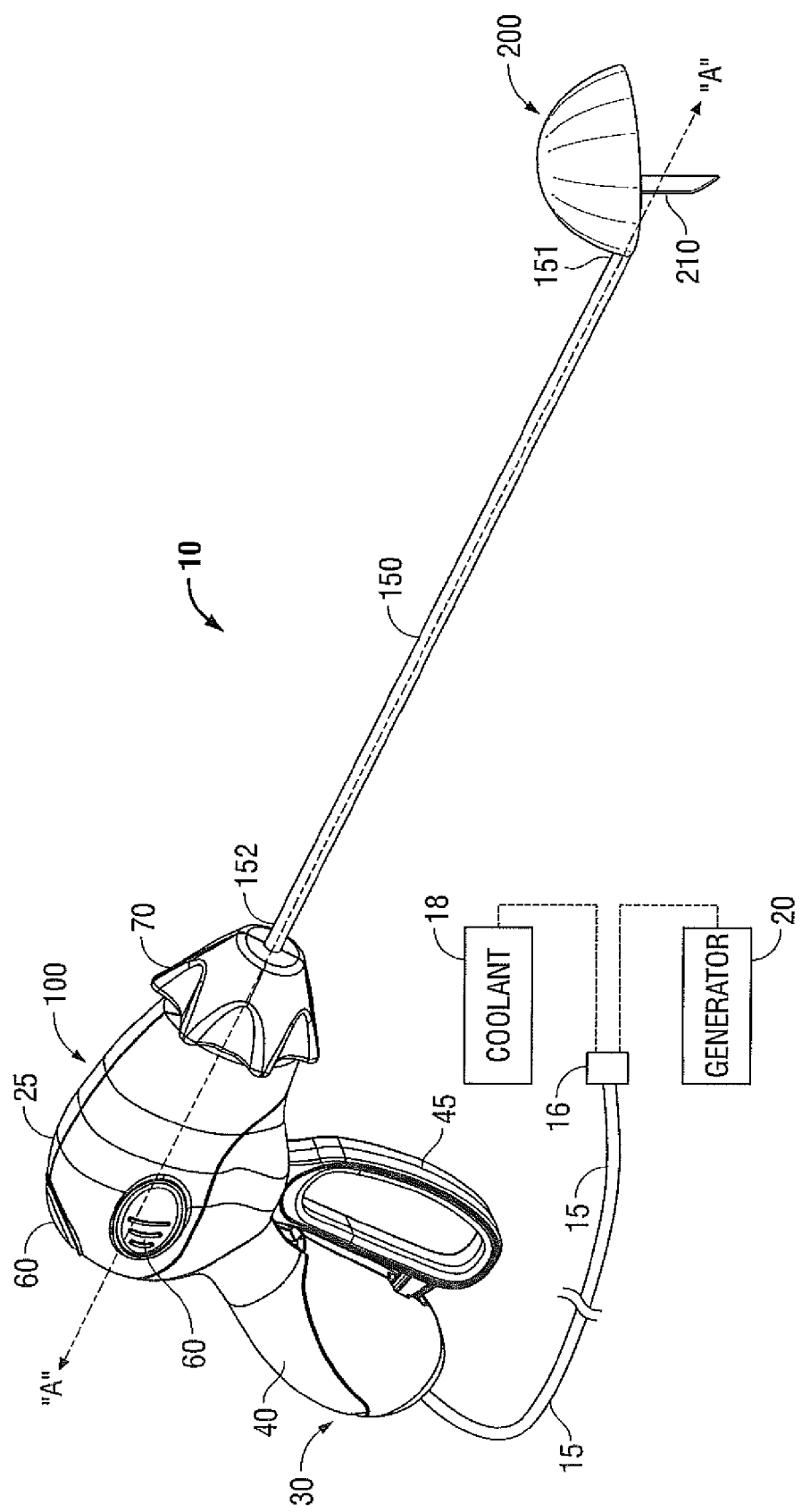
FIG. 1 shows a diagram of an embodiment of an ablation system that includes an ablation instrument having a microwave aperture and a retractable blade in accordance with an embodiment of the present disclosure.
Figure 2:
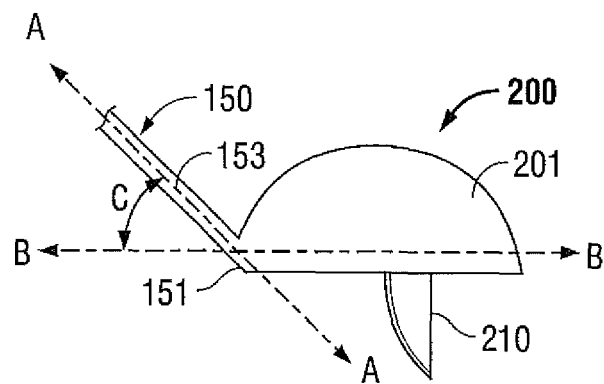
FIG. 2 shows a side view of an embodiment of a microwave aperture having a retractable blade in an extended position in accordance with an embodiment of the present disclosure.
Figure 3:
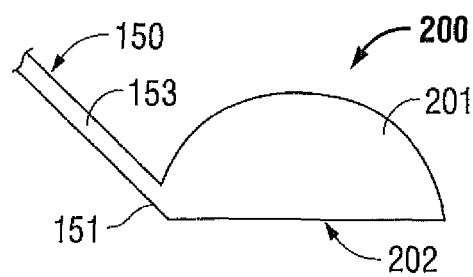
FIG. 3 shows a side view of an embodiment of a microwave aperture having a retractable blade in an retracted position in accordance with an embodiment of the present disclosure.
Figure 4:
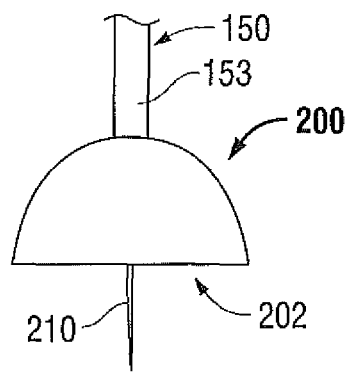
FIG. 4 shows a distal view of an embodiment of a microwave aperture having a retractable blade in an extended position in accordance with an embodiment of the present disclosure.
Figure 5:
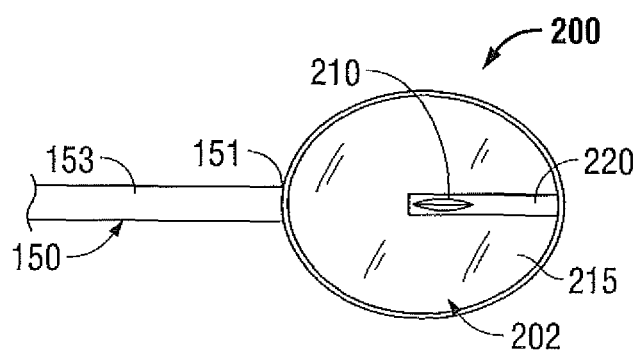
FIG. 5 shows a bottom view of an embodiment of a microwave aperture having a retractable blade in an extended position in accordance with an embodiment of the present disclosure.

Particular embodiments of the present disclosure are described hereinbelow with reference to the accompanying drawings; however, it is to be understood that the disclosed embodiments are merely examples of the disclosure, which may be embodied in various forms. Well-known functions or constructions and repetitive matter are not described in detail to avoid obscuring the present disclosure in unnecessary or redundant detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the term "proximal," as is traditional, shall refer to the end of the instrument that is closer to the user, while the term "distal" shall refer to the end that is farther from the user. In addition, as used herein, terms referencing orientation, e.g., "top", "bottom", "up", "down", "left", "right", "clockwise", "counterclockwise", and the like, are used for illustrative purposes with reference to the figures and features shown therein. It is to be understood that embodiments in accordance with the present disclosure may be practiced in any orientation without limitation.

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As it is used in this description, "ablation procedure" generally refers to any ablation procedure, such as microwave ablation, radio frequency (RF) ablation, or microwave ablation assisted resection. As it is used in this description, "transmission line" generally refers to any transmission medium that can be used for the propagation of signals from one point to another.

Various embodiments of the present disclosure provide electrosurgical devices operably associated with directional reflector assemblies for treating tissue and methods of directing electromagnetic radiation to a target volume of tissue. Embodiments may be implemented using electromagnetic radiation at microwave frequencies, or, at other frequencies. An electrosurgical system having an aperture assembly that includes an energy applicator operably associated with a directional reflector assembly, according to various embodiments, is configured to operate between about 300 MHz and about 10 GHz with a directional radiation pattern.

Various embodiments of the presently disclosed electrosurgical devices, directional reflector assemblies, thereto and electrosurgical system including the same are suitable for microwave ablation and for use to pre-coagulate tissue for microwave ablation assisted surgical resection. Although various methods described hereinbelow are targeted toward microwave ablation and the destruction and/or resection of targeted tissue, it is to be understood that methods for directing electromagnetic radiation may be used with other therapies in which the target tissue is partially destroyed, damaged, or dissected, such as, for example, to prevent the conduction of electrical impulses within heart tissue. In addition, the teachings of the present disclosure may apply to a dipole, monopole, helical, or other suitable type of microwave antenna.

FIG. 1 shows an ablation system 10 in accordance with an embodiment of the present disclosure. The ablation system 10 includes an ablation instrument 100 that is operably connected by a cable 15 to connector 16, which further operably connects instrument 100 to a generator assembly 20. Generator assembly 20 may be a source of ablation energy, e.g., microwave or RF energy in the range of about 915 MHz to about 10.0 GHz. Instrument 100 is adapted for use in various surgical procedures and generally includes a housing 25, a handle assembly 30, an ablation energy actuator 60, and a rotating assembly 70. Instrument 100 includes a shaft 150 having an aperture assembly 200 coupled to a distal end 151 of the shaft. A proximal end 152 of shaft 150 mechanically engages the housing 25. Aperture assembly 200 is configured to enable the simultaneous dissection and coagulation of tissue. Cable 15 may additionally or alternatively provide a conduit (not explicitly shown) configured to provide coolant from a coolant source 18 to ablation instrument 100.

Handle assembly 30 includes a proximal stationary handle 40 and a distal movable handle 45. Movable handle 45 is operably coupled to a retractable blade 210 to facilitate the selective extension and retraction of blade 210 with respect to aperture assembly 200. Blade 210 may include a cutting edge on a proximal edge thereof (as referenced with blade 210 in a fully extended position), on a distal edge thereof, and/or both edges thereof. Blade 210 may additionally or alternatively include serrations, saw teeth, or other cutting instrumentalities. In an embodiment, blade 210 may include a scissors, bypass cutter, or anvil cutter, which may be extended and retracted by a first actuator and pull wire combination, and actuated for cutting by a second actuator and pull wire combination.

An ablation energy actuator 60 is operably coupled to generator 20 to enable a user, e.g., a surgeon, to selectively activate and de-activate the delivery of ablation energy to patient tissue. Rotating assembly 70 is operably coupled to a proximal end 152 of shaft 150 to facilitate the rotation of shaft 150 about the longitudinal axis "A" thereof, thereby facilitating the rotation of aperture assembly 200, which enables a user, e.g., a surgeon, to position aperture assembly 200 in varying orientations to accommodate surgical requirements.

FIGS. 2-5 show an embodiment of an ablation instrument 100 having a shaft assembly 150 and an aperture assembly 200 disposed at the distal end 151 of the shaft 150. In the illustrated embodiment, the aperture assembly 200 is generally hemispherical in shape, having a closed upper portion 201, and an open bottom portion 202 having a substantially planar shape. While, as shown, upper portion 201 of aperture assembly 200 is generally hemispherical in shape, other shapes are contemplated without departing from the sprit and scope of the present disclosure, including without limitation, a generally elongated hemispherical shape, a generally clamshell shape, a generally semicylindrical shape, a generally parabolic shape, and/or a generally conical shape.

Shaft assembly 150 includes a coaxial feedline 153 having in an inner conductor 152, a dielectric 160 coaxially disposed about the inner conductor 152 and an outer conductor 155 coaxially disposed about the dielectric 160. Inner conductor 152 and outer conductor 155 may be formed from any suitable heat-resistant metallic material, including without limitation stainless steel. At a distal end 151 of the shaft assembly 150, the inner conductor 152 extends beyond the outer conductor 155 and is operably coupled to a radiating section 208. The outer conductor 155 is operably joined at a distal end 151 of shaft assembly 150 to a reflector 205. In embodiments, the reflector 205 may be joined to outer conductor 155 such that the horizontal axis "B" of aperture assembly 200 is angled with respect to the longitudinal axis "A" of shaft 150, as shown. The angular offset "C" between shaft assembly 150 and aperture 200 may provide improved ergonomics and ease the manipulation of the instrument 100 during use. Outer conductor 155 is electromechanically joined to reflector 205 at a junction 207. Outer conductor 155 and reflector 205 may be joined by any suitable manner of attachment, including without limitation, welding, brazing, and/or threaded coupler. In an embodiment, outer conductor 155 and reflector 205 may be integrally formed.

A generally planar radiofrequency-transparent bottom cover 215 is disposed on open bottom 202 of reflector 205. Bottom cover 215 is fixed to reflector 205 along a bottom perimeter 203 thereof using any suitable manner of fixation, e.g., adhesive, mechanical crimp, retaining collar (not explicitly shown), threaded fasteners, rivets, and injection overmolding. Bottom cover 215 may be formed from any suitable heat-resistant material that is transparent to microwave or RF energy in the operating range of about 915 MHz to about 10.0 GHz, such as without limitation, polymeric materials, polyglass composite (e.g., fiberglass), carbon fiber, and the like. An opening 220 is defined within bottom cover 202 and is dimensioned to permit blade 210 to extend therethrough. As shown, opening 220 has an elongated rectangle shape; however, opening 220 may have any shape suitable to accommodate the extension and retraction of blade 210.

Figure 6:
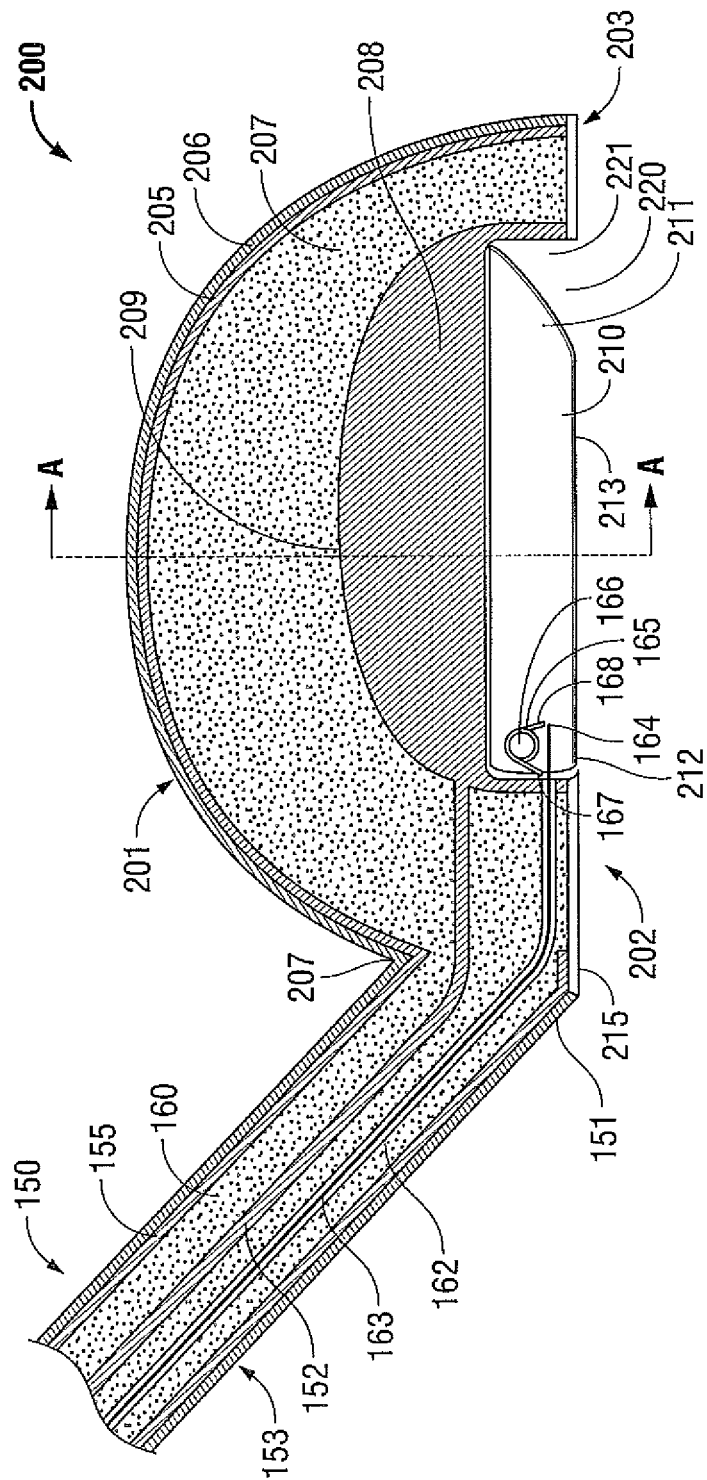
FIG. 6 shows a side, cutaway view of an embodiment of a microwave aperture having a retractable blade in a retracted position in accordance with an embodiment of the present disclosure.
Figure 7:
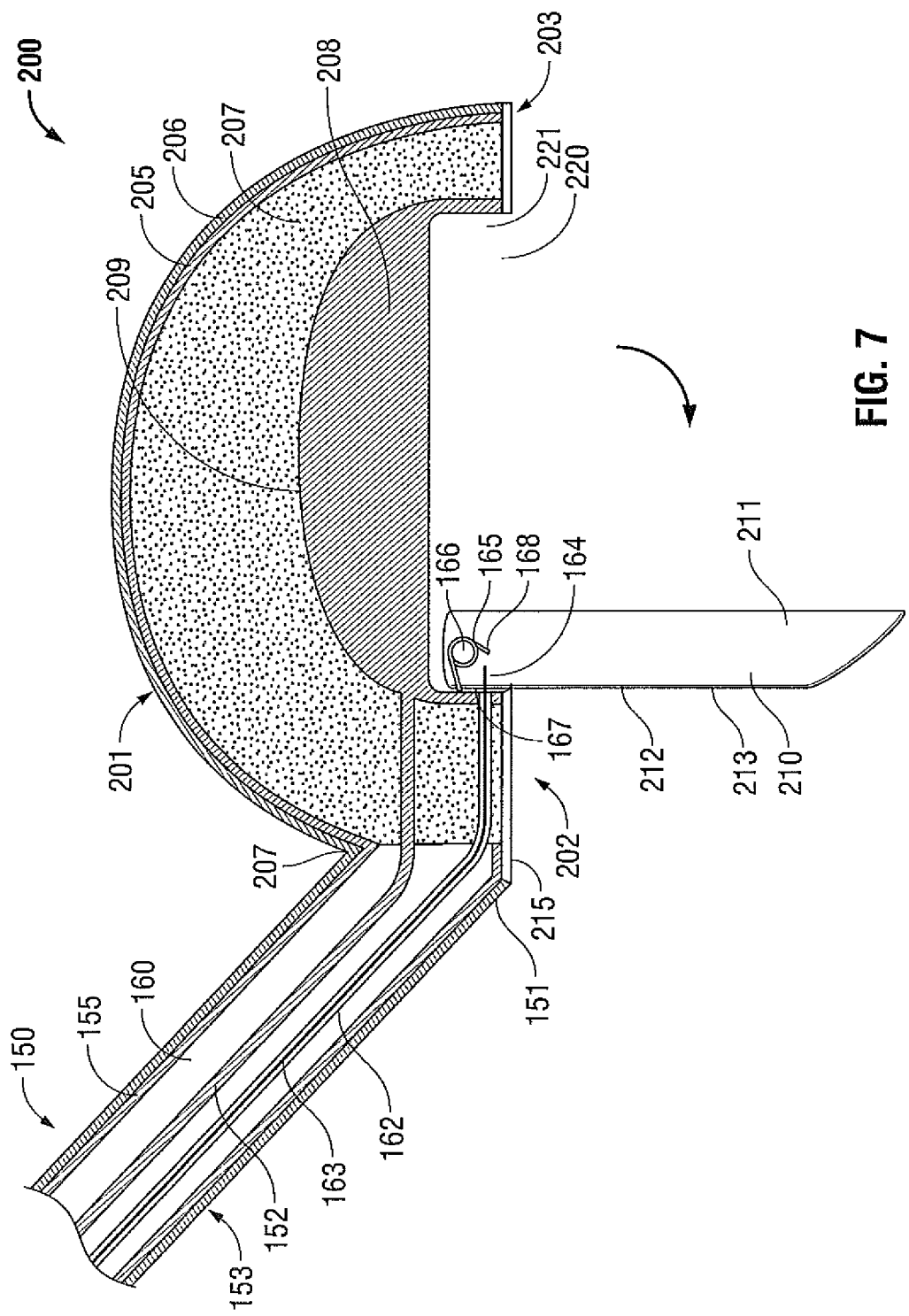
FIG. 7 shows a side, cutaway view of an embodiment of a microwave aperture having a retractable blade in an extended position in accordance with an embodiment of the present disclosure.
Figure 8:
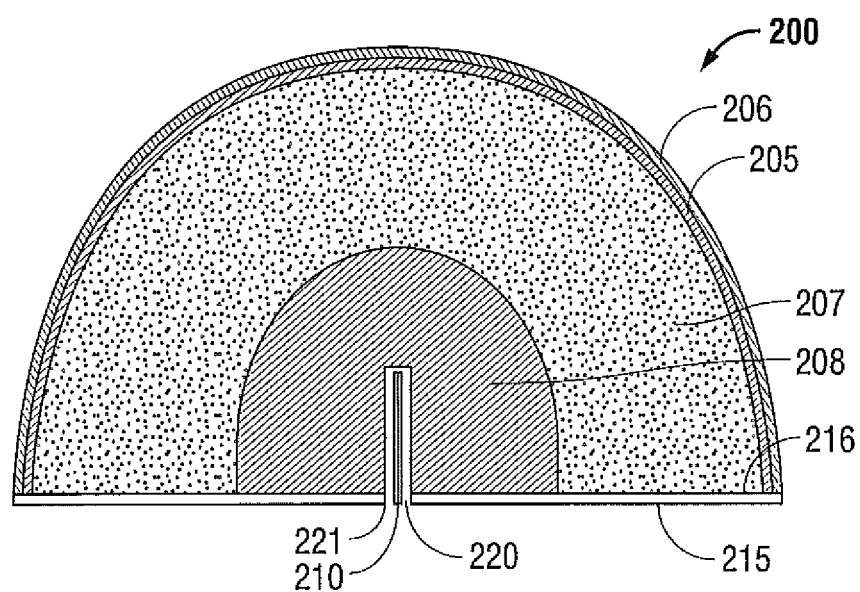
FIG. 8 shows a distal, section view of an embodiment of a microwave aperture having a retractable blade in a retracted position in accordance with an embodiment of the present disclosure.

With reference to FIGS. 6, 7, and 8, blade 210 is disposed within a cavity 221 defined within the radiating section 208. Blade 210 is pivotably mounted about a transversely-oriented pivot pin 166 disposed the radiating section 208, the reflector 201, or a dielectric region 207, and is movable between a closed, or retracted position as shown in FIG. 6, and an open, or extended position as seen in FIG. 7. Blade 210 may be formed from any suitable metallic or non-metallic material, including without limitation, stainless steel, ceramic, or polymeric materials. In an embodiment, blade 210 is formed from polyether ether ketone (PEEK).

A biasing member 165 is configured to bias blade 210 toward a closed position. As shown, biasing member 165 may be a V-spring, having a coil base coaxially positioned on pin 166, a first movable leg joined to blade 210 at a blade mounting point 168 and a second stationary leg that bears against a stationary mounting point 167 such that blade 210 is biased toward a closed position, e.g., counterclockwise as seen in FIGS. 6 and 7. It should be understood that the biasing member 165 disclosed herein is not limited to a V-spring, and may include any suitable source of biasing force, including without limitation a coil spring, a leaf spring, a gas spring, a pressure- or vacuum-actuated device, an elastomeric spring, magnetic or electromagnetic devices, a shape memory alloy motor, and other sources of biasing force as will be familiar to the skilled practitioner. Additionally or alternatively, the biasing member 165 may be integrally formed with, for example, blade 210, radiating section 208, etc.

In the example embodiment depicted in FIGS. 6, 7, and 8, blade 210 is deployed (e.g., opened or extended) using a pull wire arrangement. A pull wire 163 extends within a wire conduit 162, having a proximal end that is operably coupled to an actuator (not explicitly shown) included in the instrument housing 25, and a distal end that is coupled to blade 210 at a mounting point 164. As shown, wire conduit 162 is routed within shaft assembly 150; however, the wire conduit may be routed externally of the shaft assembly, e.g., along a surface of shaft assembly, as shown in the embodiment depicted in FIGS. 9 and 10.

During use, a surgeon may deploy blade 210 by actuating a control, e.g., handle 45, trigger 50, etc., that is operably associated with pull wire 163 and configured to draw pull wire 163 in a proximal direction upon actuation. The proximal motion of pull wire 163 is translated to a downward pivoting motion of blade 210, overcoming the biasing force of biasing member 165 and causing blade 210 to swing downward into an extended position as best seen in FIG. 7. In an embodiment, the actuator may include a locking mechanism (not explicitly shown) that engages when blade 210 reaches an open position and that retains blade 210 in the open position until unlocked. Conversely, to close the blade 210, a surgeon may release or relax the control, e.g., handle 45, which, in turn, allows the biasing force of biasing member 165 to return blade 210 to its resting, e.g., closed position. Pull wire 163 may be drawn distally as blade 210 rotates to a rest position as best seen in FIG. 6.

While the example embodiments herein illustrate a pull wire actuation mechanism, other suitable actuation mechanisms may be utilized without departing from the spirit and scope of the present disclosure, including without limitation, rod actuation, shaft actuation, gear actuation, hydraulic actuation, electromechanical actuation, shape memory alloy actuation, thermal expansion actuation, and the like.

Aperture assembly 200 includes a dielectric region 207 that is generally contained within a volume defined by the interior of reflector 205, an upper surface 209 of radiating section 208, and an upper surface 216 of bottom cover 215. Any suitable heat-resistant material having dielectric (e.g., electrically non-conductive) properties may be utilized to form dielectric region 207, including without limitation, polymeric material and/or ceramic material. In embodiments, dielectric region 207 may include two or more dielectric layers. In yet other embodiments, dielectric region 207 may include liquid, such as water.

Shaft 150 and/or aperture 200 may include a lubricious coating 153, 201, respectively, on an outer surface thereof, that may reduce the undesirable adhesion of biomaterials thereto. Coating 153 and/or coating 201 may be formed from any suitable biocompatible and heat-resistant lubricious material, such as without limitation, polytetrafluoroethylene (a.k.a. PTFE or Teflon®, manufactured by the E.I. du Pont de Nemours and Co. of Wilmington, Del., USA), polyethylene tephthalate (PET), chemical vapor deposited poly(p-xylylene) polymer (e.g., parylene), and the like.

Figure 9:
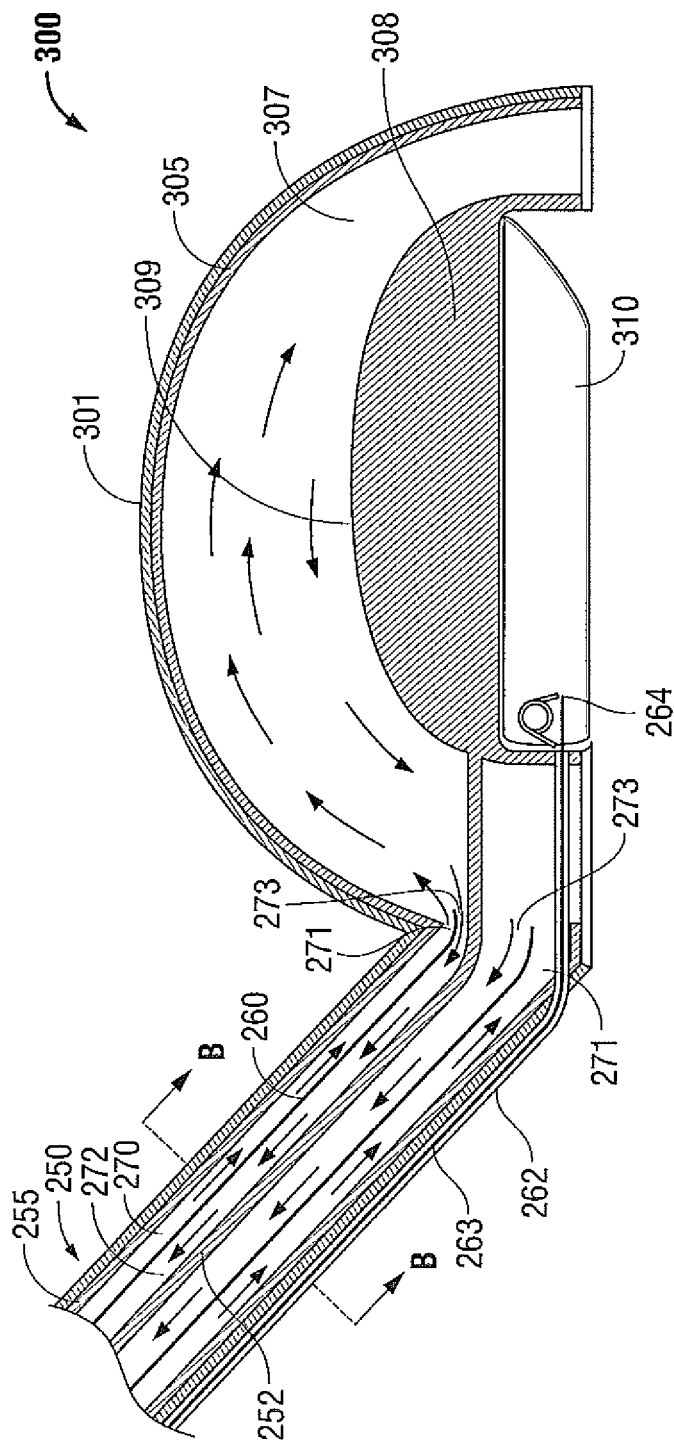
FIG. 9 shows a side, cutaway view of an embodiment of a liquid-cooled microwave aperture having a retractable blade in a retracted position in accordance with an embodiment of the present disclosure.
Figure 10:
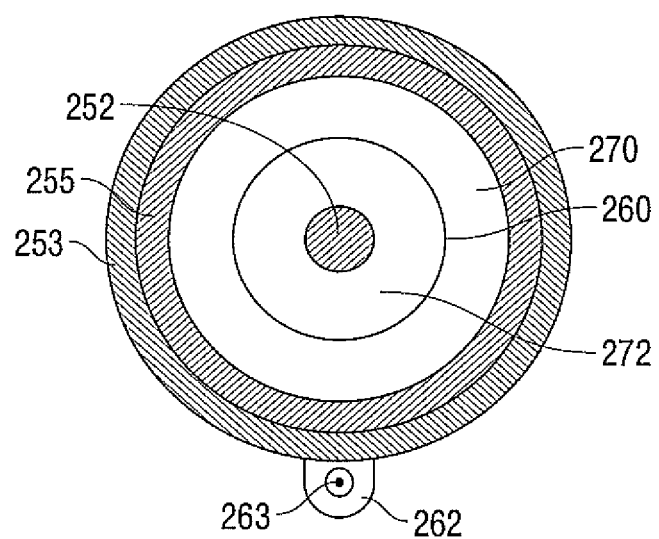
FIG. 10 shows a section view of an embodiment of a shaft having a coolant conduit in accordance with an embodiment of the present disclosure.

In another example embodiment best illustrated in FIGS. 9 and 10, an aperture assembly 300 includes a liquid-cooling dielectric chamber 307. A shaft 250 includes an inner conductor 252 that is electromechanically operably coupled at a distal end thereof to a radiating section 308 and an outer conductor 255 that is electromechanically coupled to a reflector 305. Shaft 250 includes a generally tubular divider 260 that is concentrically disposed between inner conductor 252 and outer conductor 255, and having a radius dimensioned to form an inflow conduit 270 and an outflow conduit 272. To accommodate the balanced distribution of coolant flow into and out of dielectric chamber 307, the cross sectional area of inflow conduit 270 and outflow conduit 272 may be about equal in size. Inflow conduit 270 includes an open distal end 271 that is configured to deliver coolant fluid to dielectric chamber 307. Inflow conduit 270, at a proximal end thereof (not explicitly shown), may be in fluid communication with a coolant source 18, such as without limitation a coolant pump or drip bag. Any suitable medium may be used as a coolant. In embodiments, deionized water, sterilized water, or saline may be used as a coolant. In one aspect, the coolant may have dielectric properties that may provide improved ablation volume and shape, and/or may provide improved impedance matching between the aperture 300 and tissue.

During use, coolant flows distally though inflow conduit 270 and is introduced into dielectric chamber 308 at an open distal end 271 of inflow conduit 270, whereupon coolant circulates through dielectric chamber 308 and exits dielectric chamber 308 though an open distal end 273 of outflow conduit 272. A fluid evacuation pump (not explicitly shown) operably coupled to a proximal end of outflow conduit 272 may be employed to assist the evacuation of coolant from dielectric chamber 208. In embodiments, the relative positions of inflow conduit 270 and outflow conduit 272 may differ from that described hereinabove, e.g., reversed (outflow conduit 272 may be defined coaxially around inflow conduit 270), or defined by one or more longitudinal ribs extending from inner conductor 252 to outer conductor 255, without departing from the spirit and scope of the present disclosure.

A pull wire 263 extends within a wire conduit 262, and includes a proximal end that is operably coupled to an actuator (not explicitly shown) operatively associated with the instrument housing 25, and a distal end that is coupled to blade 210 at a mounting point 264. As shown, wire conduit 262 is routed along a surface of shaft assembly 250, however, a wire conduit may be routed within shaft assembly 250, e.g., as shown in the FIG. 6 embodiment.

Figure 11:
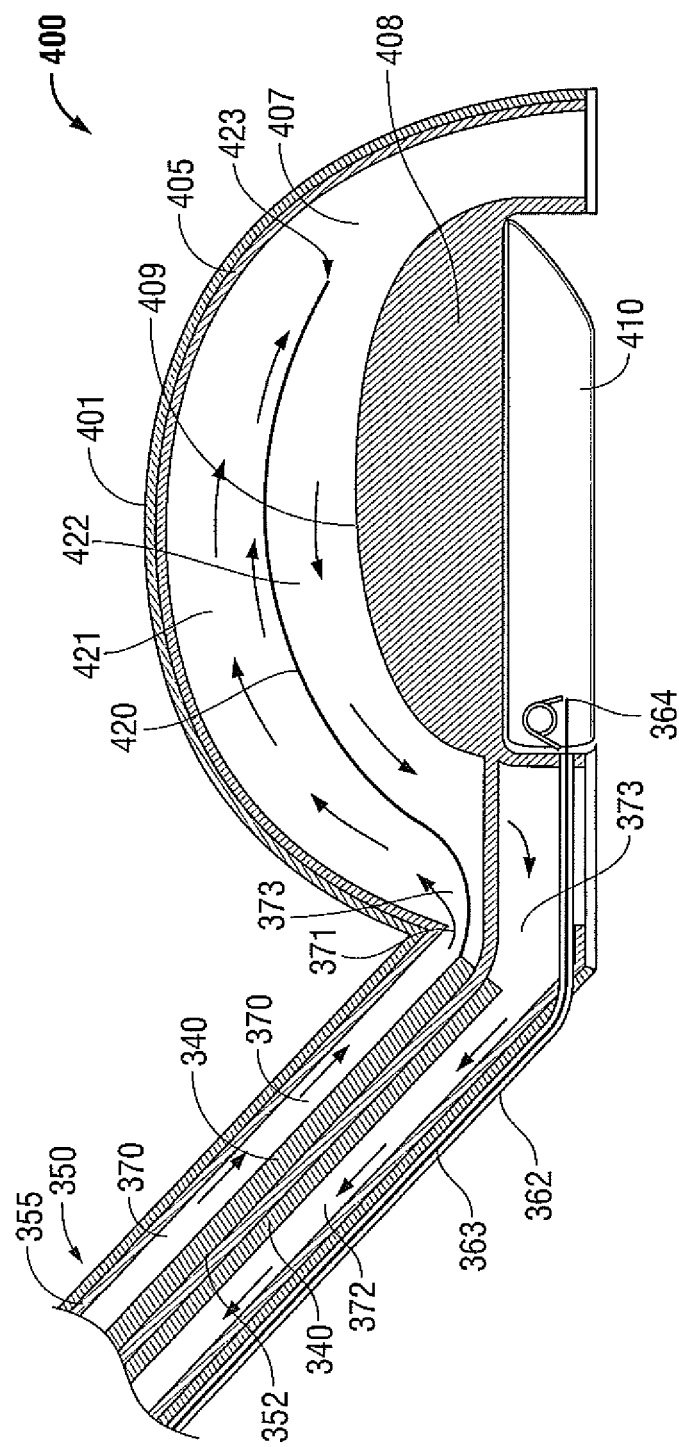
FIG. 11 shows a side, cutaway view of another embodiment of a liquid-cooled microwave aperture having a baffle in accordance with an embodiment of the present disclosure.

Another embodiment in accordance with the present disclosure is presented in FIG. 11. An aperture assembly 400 includes a liquid-cooling dielectric chamber 407 having a baffle 420 disposed therein. Baffle 420 is configured to define an inflow dielectric region 421 and an outflow dielectric region 422 within dielectric region 407. A shaft 350 includes an inner conductor 352 that is electromechanically operably coupled at a distal end thereof to a radiating section 408 and an outer conductor 355 that is electromechanically coupled to a reflector 405. Shaft 350 includes an inflow conduit 370 and an outflow conduit 372 defined therein along a longitudinal axis thereof. A dielectric 340 is coaxially disposed about inner conductor 352 and extends distally to dielectric chamber 407. Baffle 420 is joined at a proximal end thereof to dielectric 340. Baffle 420 and dielectric 340 may be joined by any suitable manner of attachment, including without limitation adhesive, welding, threaded coupling, crimping, and/or overmolding. In an embodiment, baffle 420 and dielectric 340 may be integrally formed. During use, coolant may be delivered from a source of coolant (not explicitly shown) via inflow conduit 370 into an inflow dielectric region 421 of dielectric chamber 407. Coolant may flow within chamber 407 in a generally distal direction within inflow dielectric region 421, to a distal end 423 of baffle 420, in a generally proximal direction within outflow dielectric region 422, and proximally through outflow conduit 372. Coolant may additionally or alternatively be circulated in a reverse-flow manner, e.g., introduced into outflow region 422 via outflow conduit 372, flowing distally within outflow conduit 372 toward a distal end 423 of baffle 420, then flowing proximally through inflow region 421 and inflow conduit 370.

Figure 12:
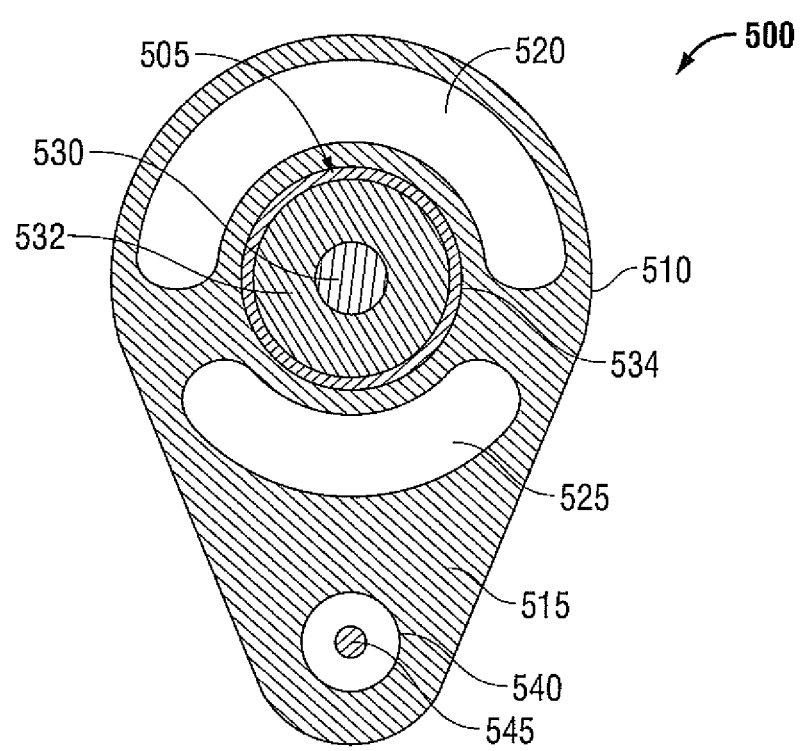
FIG. 12 shows a section view of an embodiment of a shaft in accordance with the present disclosure.

Yet another embodiment of a shaft 500 in accordance with the present disclosure is illustrated in the cross-sectional view of FIG. 12. Shaft 500 includes a solid body 515 which may be formed from any suitable high strength, heat resistant material, including without limitation stainless steel, fiber-reinforced plastic, carbon fiber, fiberglass-epoxy composite, and the like. Shaft 500 includes a first fluid conduit 520 and a second fluid conduit 525 defined therethrough along a longitudinal axis of the shaft 500. First fluid conduit 520 and/or second fluid conduit 525 may be adapted to circulate a coolant from a source of coolant (not explicitly shown), within the shaft 500, and/or within an aperture assembly as disclosed herein. As shown, first fluid conduit 520 and/or second fluid conduit 525 have a generally arcuate cross section, however it is contemplated within the scope of the present disclosure that first fluid conduit 520 and/or second fluid conduit 525 may include any suitable cross-sectional shape. Shaft 500 includes a wire conduit 540 defined therethrough along a longitudinal axis thereof that is dimensioned to accommodate a pull wire 545 disposed therein. Pull wire 545 may be configured to actuate a retractable blade assembly as disclosed herein.

Shaft 500 includes a coaxial feedline 505 disposed along a longitudinal axis of the shaft 500. Coaxial feedline 505 includes an inner conductor 530, a dielectric 532 coaxially disposed about the inner conductor 530, and an outer conductor 534 coaxially disposed about the dielectric 532.

The described embodiments of the present disclosure are intended to be illustrative rather than restrictive, and are not intended to represent every embodiment of the present disclosure. It is to be understood that the steps of a method provided herein may be performed in combination and/or in a different order than presented herein without departing from the scope and spirit of the present disclosure. Further variations of the above-disclosed embodiments and other features and functions, or alternatives thereof, may be made or desirably combined into many other different systems or applications without departing from the spirit or scope of the disclosure as set forth in the following claims both literally and in equivalents recognized in law.

What is claimed is:

1. A surgical instrument, comprising:
   a housing having an actuator operatively associated therewith;
   a shaft extending distally from the housing, the shaft including:
      a feedline having an inner conductor;
      an outer conductor disposed coaxially about the inner conductor;
      a wire conduit disposed along a longitudinal axis of the shaft; and
      a pull wire disposed within the wire conduit and having a proximal and a distal end, wherein a proximal end of the pull wire is operably coupled to the actuator; and
   an aperture assembly coupled to a distal end of the shaft, the aperture assembly including:
      a reflector operably coupled to the outer conductor and having a closed hemispherical shaped upper portion and an open lower portion;
      an antenna disposed within the reflector and operably coupled to the inner conductor;
      a blade mounted within the reflector and pivotable between at least a closed position and an open position, wherein a distal end of the pull wire is operably coupled to the blade; and
      a bottom cover enclosing the open lower portion of the reflector.

2. The surgical instrument in accordance with claim 1, wherein the wire conduit is disposed within the shaft.

3. The surgical instrument in accordance with claim 1, wherein the wire conduit is disposed on an outer surface of the shaft.

4. The surgical instrument in accordance with claim 1, further comprising a biasing member configured to bias the blade toward the closed position.

5. The surgical instrument in accordance with claim 1, wherein the bottom cover is constructed from radiofrequency-transparent material.

6. The surgical instrument in accordance with claim 1, the housing further comprising a rotating assembly operably coupled to a proximal end of the shaft and configured to facilitate the rotation of the shaft about a longitudinal axis thereof.

7. The surgical instrument in accordance with claim 1, further comprising a lubricious coating disposed on at least one of an outer surface of the shaft or an outer surface of the closed upper portion of the reflector.

8. The surgical instrument in accordance with claim 7, wherein the lubricious coating is formed from material selected from the group consisting of polytetrafluoroethylene, polyethylene tephthalate, and parylene.

9. The surgical instrument in accordance with claim 1, further comprising a dielectric region disposed between an inner surface of the reflector and the antenna.

10. The surgical instrument in accordance with claim 1, wherein the shaft further includes a tubular divider concentrically disposed between the inner conductor and the outer conductor to form an inflow conduit and an outflow conduit.

11. The surgical instrument in accordance with claim 10, wherein a distal opening of at least one of the inflow conduit and the outflow conduit are in fluid communication with an internal volume of the reflector.

12. The surgical instrument in accordance with claim 10, wherein a proximal end of the inflow conduit is adapted to operably couple to source of coolant.

13. The surgical instrument according to claim 1, wherein the blade is disposed within the open lower portion when the blade in the closed position and extends at least partially from the open lower portion when the blade is in the open position.

14. The surgical instrument according to claim 1, wherein the inner conductor is operably coupled to a radiating section disposed within the reflector.

15. The surgical instrument according to claim 14, wherein the blade is disposed within a cavity defined within the radiating section when the blade is in the closed position.

16. A surgical ablation system, comprising:
    a source of microwave ablation energy;
    a surgical instrument operably coupled to the source of ablation energy, the instrument comprising:
       a housing having an actuator operatively associated therewith;
       a shaft extending distally from the housing, the shaft including:
          a feedline having an inner conductor;
          an outer conductor disposed coaxially about the inner conductor;
          a wire conduit disposed along a longitudinal axis of the shaft; and
          a pull wire disposed within the wire conduit and having a proximal and a distal end, wherein a proximal end of the pull wire is operably coupled to the actuator; and
       an aperture assembly coupled to a distal end of the shaft, the aperture assembly including:
          a reflector operably coupled to the outer conductor and having a closed hemispherical shaped upper portion and an open lower portion;
          an antenna disposed within the reflector and operably coupled to the inner conductor;
          a blade mounted within the reflector and pivotable between at least a closed position and an open position, wherein a distal end of the pull wire is operably coupled to the blade; and a bottom cover enclosing the open lower portion of the reflector.

17. The surgical ablation system in accordance with claim 16, wherein the instrument housing further comprises a rotating assembly operably coupled to a proximal end of the shaft and configured to facilitate the rotation of the shaft about a longitudinal axis defined by the shaft.

18. The surgical ablation system in accordance with claim 16, wherein the shaft further includes a tubular divider concentrically disposed between the inner conductor and the outer conductor to form an inflow conduit and an outflow conduit.

19. The surgical ablation system in accordance with claim 18, further comprising a source of coolant adapted to operably couple to the inflow conduit.

20. The surgical ablation system in accordance with claim 18, further comprising a fluid evacuation pump operably coupled to the outflow conduit.

\* \* \* \* \*